(12) United States Patent
Lia et al.

(10) Patent No.: US 8,459,844 B2
(45) Date of Patent: Jun. 11, 2013

(54) REPLACEMENT LIGHT ASSEMBLY

(75) Inventors: Raymond A. Lia, Auburn, NY (US);
Ervin Goldfain, Syracuse, NY (US);
Chris R. Roberts, Skaneateles, NY (US); Steven R. Slawson, Camillus, NY (US); Robert J. Wood, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 392 days.

(21) Appl. No.: 12/828,760

(22) Filed: Jul. 1, 2010

(65) Prior Publication Data
US 2012/0002422 A1    Jan. 5, 2012

(51) Int. Cl.
*F21V 5/04* (2006.01)
*F21V 5/00* (2006.01)

(52) U.S. Cl.
USPC .......................................... 362/326; 362/336

(58) Field of Classification Search
USPC ................................................ 362/326–340
See application file for complete search history.

(56) References Cited

U.S. PATENT DOCUMENTS

| | | | |
|---|---|---|---|
| 1,828,777 A | 10/1931 | Leventhal | |
| 2,027,663 A | 1/1936 | Allyn | |
| 4,234,910 A | 11/1980 | Price | |
| 4,464,608 A | 8/1984 | Pilley | |
| 4,514,476 A | 4/1985 | Fitzgerald | |
| 4,527,552 A | 7/1985 | Hattori | |
| 4,643,546 A | 2/1987 | Richards | |
| 4,699,482 A | 10/1987 | Utsugi | |
| 4,710,002 A | 12/1987 | Pomerantzeff | |
| 4,834,528 A | 5/1989 | Howland et al. | |
| 5,144,190 A | 9/1992 | Thomas et al. | |
| 5,144,495 A | 9/1992 | Merton et al. | |
| 5,419,312 A | 5/1995 | Arenberg et al. | |
| 5,430,509 A | 7/1995 | Kobayashi | |
| 5,450,144 A | 9/1995 | Ben Nun | |

(Continued)

FOREIGN PATENT DOCUMENTS

| FR | 2773701 | 7/1999 |
|---|---|---|
| GB | 1244529 | 9/1971 |

(Continued)

OTHER PUBLICATIONS

Blair, Frank W.: Activities of the Chihuahua Deer-Mouse in Relation to Light Intensity; Journal of Wildlife Management; vol. 7; No. 1; Jan. 1943; pp. 92-97.

(Continued)

*Primary Examiner* — Karabi Guharay
*Assistant Examiner* — Nathaniel Lee

(57) ABSTRACT

A light assembly for a hand-held medical diagnostic instrument. The light assembly includes a substrate having a top surface and a bottom surface, a light source mounted to the top surface, and the bottom surface having first and second electrical terminals. The light assembly further includes a circuit board disposed inclined to the substrate, the circuit board having first and second electrical terminals, a first connector mounting and electrically connecting the first electrical terminal of the substrate to the first electrical terminal of the circuit board, a second connector mounting and electrically connecting the second electrical terminal of the substrate to the second electrical terminal of the circuit board, a heat sink, and a thermal conductor thermally connecting at least one of the first and second electrical terminals of the substrate to the heat sink.

25 Claims, 12 Drawing Sheets

U.S. PATENT DOCUMENTS

| | | | |
|---|---|---|---|
| 5,500,698 A | 3/1996 | Sims | |
| 5,512,966 A | 4/1996 | Snook | |
| 5,568,208 A | 10/1996 | Van de Velde | |
| 5,568,209 A | 10/1996 | Priester et al. | |
| 5,614,966 A | 3/1997 | Iijima et al. | |
| 5,734,459 A | 3/1998 | Chang | |
| 5,838,421 A | 11/1998 | Pedack | |
| 5,841,509 A | 11/1998 | Harooni et al. | |
| 5,861,939 A | 1/1999 | Heacock | |
| 5,886,770 A | 3/1999 | Damato | |
| 5,887,965 A | 3/1999 | Edens et al. | |
| 5,919,130 A | 7/1999 | Monroe et al. | |
| 6,003,993 A | 12/1999 | Webb | |
| 6,142,629 A | 11/2000 | Adel et al. | |
| 6,158,863 A | 12/2000 | Afran | |
| 6,318,887 B1 | 11/2001 | Matsumoto | |
| 6,340,868 B1 | 1/2002 | Lys et al. | |
| 6,361,167 B1 | 3/2002 | Su et al. | |
| 6,368,270 B1 | 4/2002 | Takami | |
| 6,406,437 B1 | 6/2002 | Zur et al. | |
| 6,439,715 B2 | 8/2002 | Burckhardt | |
| 6,447,119 B1 | 9/2002 | Stewart et al. | |
| 6,459,919 B1 | 10/2002 | Lys et al. | |
| 6,520,640 B1 | 2/2003 | Binnun | |
| 6,550,917 B1 | 4/2003 | Neal et al. | |
| 6,595,643 B2 | 7/2003 | Levine | |
| 6,609,794 B2 | 8/2003 | Levine | |
| 6,611,320 B1 | 8/2003 | Lindberg et al. | |
| 6,637,882 B1 | 10/2003 | Goldfain et al. | |
| 6,766,042 B2 | 7/2004 | Freeman et al. | |
| 7,083,299 B2 | 8/2006 | Chapman | |
| 7,276,025 B2 | 10/2007 | Roberts et al. | |
| 7,458,934 B2 | 12/2008 | Roberts et al. | |
| 7,490,951 B2 | 2/2009 | Klipstein et al. | |
| 7,533,992 B2 | 5/2009 | Williams | |
| 7,772,786 B2 | 8/2010 | Hosoda et al. | |
| 2006/0039139 A1 | 2/2006 | Maglica et al. | |
| 2009/0287192 A1* | 11/2009 | Vivenzio et al. | 606/1 |
| 2010/0314986 A1* | 12/2010 | Gershaw | 313/46 |
| 2011/0054263 A1 | 3/2011 | Chou et al. | |

FOREIGN PATENT DOCUMENTS

| | | |
|---|---|---|
| GB | 1372646 | 11/1974 |
| GB | 2310051 | 8/1997 |
| GB | 2381305 | 8/2003 |
| GB | 2374402 | 10/2003 |
| WO | WO 89/08475 | 9/1989 |
| WO | WO 98/49931 | 11/1998 |
| WO | WO 01/60241 | 8/2001 |

OTHER PUBLICATIONS

Colvard, M: Abstract of—Preoperative Measurement of Scotopic Pupil Dilation Using an Office Pupillometer; Center for Ophthalmic Surgery; Journal of Cataract and Refractive Surgery; 1998; vol. 24, No. 12; pp. 1594-1597.

Dreher, Andreas W.: Field Portable Digital Ophthalmoscope/Fundus Camera—Final Report Nov. 6, 1996—May 5, 1997; Jun. 1997; published by Laser Diagnostic Technologies, Inc.; 25 pgs.

Ferree, C.E. et al.: Intensity of Light in Relation to the Examination of the Eye; The British Journal of Ophthalmology; 1936; pp. 331-346.

Heimel, J. et al.: SNOM/STM Using a Tetrahedral Tip and a Sensitive Current-to-Voltage Converter; Journal of Microscopy, vol. 202, Pt. I; Apr. 2001; pp. 53-59.

Kondo et al.: Recording Multifocal Electroretinograms With Fundus Monitoring; vol. 38 No. 5; Apr. 1997; published by Investigative Ophthalmology & Visual Science; pp. 1049-1052.

Neurosurgery: A Manual and Atlas of Medical Ophthalmoscopy; vol. 36(5), May 1995, Copyright © by the Library of Congress of Neurological Surgeons, pp. 1052-1056.

Schaeffel et al.: Lower-field myopia and astigmatism in amphibians and chickens; Josa A, vol. 11, Issue 2, Feb. 1994; pp. 487-495.

Talbot, S.A. et al.: A Multibeam Ophthalmoscope for the Study of Retinal Physiology; Journal of the Optical Society of America; vol. 42, No. 12; Dec. 1952; pp. 931-936.

Welch Allyn: Diagnostic Instruments (Product literature/brochure); 1984, SL 1540; 27 pgs.

Welch Allyn: Electrically Illuminated Diagnostic Instruments, Mar. 15, 1966; 17 pgs.

International Search Report and Written Opinion for International Application No. PCT/US11/27630, dated Sep. 30, 2011, 10 pages.

* cited by examiner

REPLACEMENT LIGHT ASSEMBLY

CROSS-REFERENCE TO RELATED APPLICATIONS

None.

STATEMENT REGARDING FEDERALLY SPONSORED RESEARCH OR DEVELOPMENT

Not applicable.

REFERENCE TO A "SEQUENCE LISTING"

Not applicable.

BACKGROUND OF THE INVENTION

1. Field of the Invention

This disclosure generally relates to the field of illumination, and more particularly, to a replacement light assembly for hand-held medical diagnostic instruments, such as those used in physicians' offices, healthcare facilities, or other medical environments.

2. Description of Related Art

Many hand-held medical diagnostic instruments such as otoscopes, ophthalmoscopes, and the like utilize miniature incandescent lamps, such as halogen or xenon lamps, as illumination sources. These lamps typically include a miniature filament, and are housed within the handle or the head of the instrument. The instruments may utilize one or more fiber optic bundles, lenses, mirrors, and/or other optical components to transmit light and/or other radiation from the lamp to an opening of the diagnostic instrument, thereby illuminating a medical target, such as a portion of the patient's anatomy, for examination.

Recently, however, there has been considerable interest in the field of light emitting diodes ("LEDs") as a potential substitute for such incandescent lamps. Such LEDs typically provide better illumination capabilities than the incandescent lamps discussed above, and are therefore desired for use in a variety of medical applications and other applications. Such LEDs also typically exhibit longer life, greater resistance to shock and/or impact, cooler operating temperatures, and other more desirable operating characteristics than miniature incandescent lamps. Moreover, some LEDs, such as color LEDs, may provide additional benefits over incandescent lamps such as spectral tuning, spectrally-specific illumination, and the like.

Accordingly, it may be desirable to replace the incandescent bulbs utilized in an existing hand-held diagnostic instrument with LEDs as illumination sources. There are, however, a number of significant optical, mechanical, thermal, and/or other differences between LEDs and incandescent lamps which must be considered when replacing such lamps with LEDs in known medical diagnostic instruments. For example, incandescent lamps are typically larger than LEDs, and emit light and other radiation having different optical characteristics than light emitted by LEDs. Thus, there is a need to develop a replacement light assembly which can be mechanically, optically, and electrically incorporated into, for example, existing hand-held medical diagnostic instruments without making mechanical, optical, and/or other modifications to these diagnostic instruments.

Embodiments of the present disclosure satisfy the needs noted above.

BRIEF SUMMARY OF THE INVENTION

In an exemplary embodiment of the present disclosure, a light assembly for a hand-held medical diagnostic instrument includes a substrate having a top surface and a bottom surface, a light source mounted to the top surface, and the bottom surface having first and second electrical terminals. The assembly also includes a circuit board disposed inclined to the substrate, the circuit board having first and second electrical terminals, a first connector mounting and electrically connecting the first electrical terminal of the substrate to the first electrical terminal of the circuit board, and a second connector mounting and electrically connecting the second electrical terminal of the substrate to the second electrical terminal of the circuit board. The assembly further includes a heat sink, and a conductor thermally connecting at least one of the first and second electrical terminals of the substrate to the heat sink.

In such an exemplary embodiment, the thermal conductor thermally connects the at least one electrical terminal to the heat sink via one of the first and second connectors, the thermal conductor includes an electrically insulative material, and the thermal conductor includes an epoxy substantially overlaying the circuit board and the first and second connectors. In another exemplary embodiment, the thermal conductor thermally connects the circuit board to the heat sink, and the heat sink includes a thermally conductive housing extending about the circuit board. The housing defines a chamber, and the thermal conductor substantially fills the chamber around the circuit board. In another exemplary embodiment, the heat sink includes a housing defining a longitudinal axis and a shoulder substantially perpendicular to the longitudinal axis. In such an exemplary embodiment, the assembly further includes a lens overlaying the light source, the lens contacting the shoulder and directing radiation from the light source to a target. The lens is fixed relative to the light source such that contact between the shoulder and the lens disposes the light source at a desired position along the longitudinal axis.

In another exemplary embodiment, the heat sink includes a housing defining a longitudinal axis and a keyway extending substantially parallel to the longitudinal axis. In such an exemplary embodiment, a lens is fixed relative to the light source and defines a key disposed within the keyway. The key fixes the light source at a desired radial position about the longitudinal axis. In addition, the housing includes a cylindrical outer wall, and a pin disposed on the outer wall coplanar with the longitudinal axis and the keyway. In such an exemplary embodiment, the pin is formed by the outer wall.

In another exemplary embodiment, the assembly further includes a lens fixed relative to the light source. The lens includes a concave surface receiving a radiation from the light source and one of a planar and a convex surface directing the received radiation toward a target. In such an exemplary embodiment, the planar surface is disposed at an angle relative to the substrate.

In still another exemplary embodiment, the assembly further includes a lens fixed relative to the light source. The lens includes a planar surface receiving radiation from the light source, and one of a planar surface and a convex surface directing the received radiation toward the target. In such an exemplary embodiment, the planar surface is disposed at an angle relative to the substrate. In still a further exemplary embodiment, the assembly further includes a lens fixed relative to the light source. The lens includes a saddle-shaped surface receiving radiation from the light source and a planar surface directing the received radiation toward a target. In such an exemplary embodiment, the planar surface is disposed at an angle relative to the substrate. In still another exemplary embodiment, the assembly further includes a lens defining a first surface receiving, radiation from the light source, a second surface directing the received radiation toward a target, and a mounting surface fixed to the substrate.

In another exemplary embodiment of the present disclosure, a method of manufacturing a light assembly for a hand-held medical diagnostic instrument includes providing an LED mounted to a substrate, the substrate having a pair of electrical terminals. The method further includes mounting and electrically connecting the electrical terminals of the substrate to corresponding electrical terminals of a circuit board of the light assembly, and thermally connecting the electrical terminals of the substrate to a heat sink of the light assembly.

In such an exemplary embodiment, the method further includes electrically insulating the electrical terminals of the substrate from the heat sink. The method also includes overlaying the electrical terminals of the substrate, the heat sink, and a portion of the circuit board with an electrically insulative thermal conductor. Such an exemplary method also includes connecting a lens to the substrate, a portion of the lens being supported by the heat sink. In such an exemplary embodiment, the heat sink includes a cylindrical housing having an open end, and the method also includes connecting an alignment pin to an outer wall of the housing at a predetermined distance from the open end. The method also includes mounting the substrate within the pinned housing.

In still a further exemplary embodiment of the present disclosure, a light assembly for a hand-held medical diagnostic instrument includes a thermally conductive cylindrical housing defining an open end, a lens disposed proximate the open end, and an LED mounted to a substrate and fixed relative to the lens, the substrate defining a pair of electrical terminals. In such an exemplary embodiment, the light assembly also includes a light assembly circuit board disposed within the housing, the electrical terminal is mounted and electrically connected to the circuit board. The light assembly further includes an electrically insulative thermal conductor thermally connecting the electrical terminals to the housing.

In a further exemplary embodiment of the present disclosure, a method of forming a lens for a hand-held medical diagnostic instrument includes providing a mold body having a first end, a second end, and a cavity between the first and second ends, the cavity configured to receive a flow of lens material. Such an exemplary method further includes connecting a first insert to the first end such that an optical surface of the first insert is fluidly connected to the cavity, the optical surface of the first insert being one of planar and concave. The method also includes connecting a second insert to the second end such that an optical surface of the second insert is fluidly connected to the cavity, the optical surface of the second insert being one of planar, concave, and saddle shape. The method further includes filling the cavity with the flow of lens material to form a lens, the optical surfaces of the first and second inserts forming corresponding optical surfaces on the lens.

DETAILED DESCRIPTION OF THE INVENTION

Figure 1:
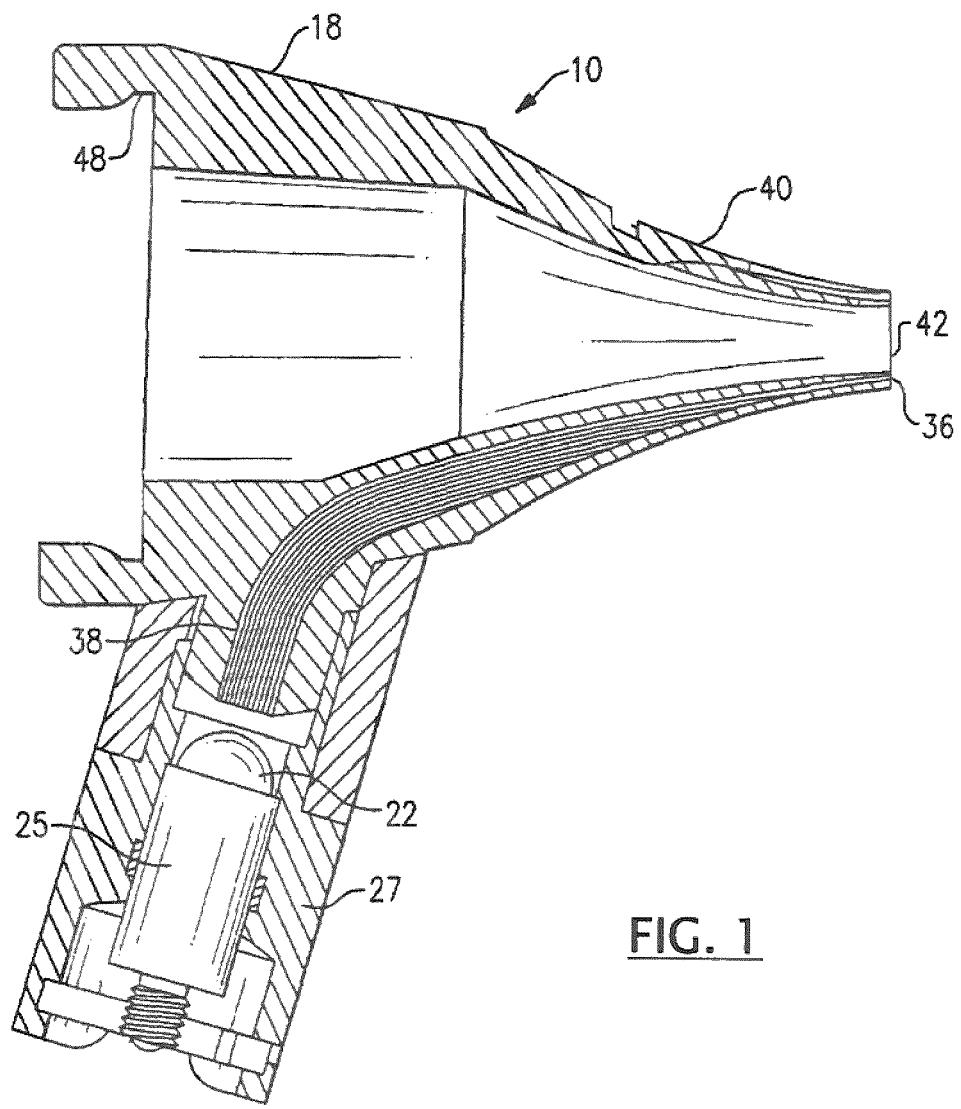
FIG. 1 is a partial side cross-sectional view of a head of an exemplary, hand-held medical diagnostic instrument.
Figure 2:
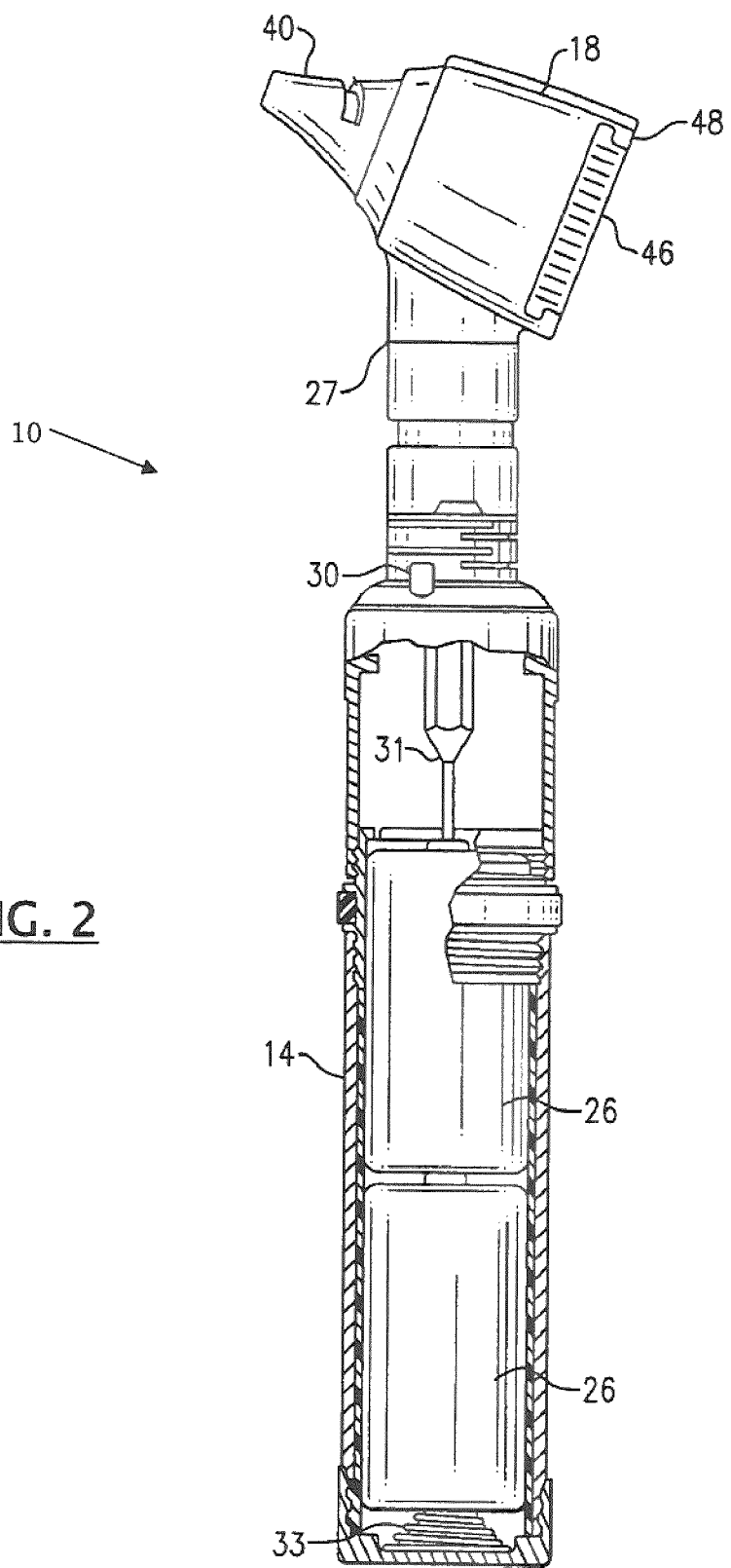
FIG. 2 is a partial side cross-sectional view of the instrument of FIG. 1.

FIGS. 1 and 2 illustrate a hand-held medical diagnostic instrument 10 according to an exemplary embodiment of the present disclosure. Embodiments of the present disclosure may be utilized with any of a variety of hand-held medical diagnostic instruments such as, for example, ophthalmoscopes, otoscopes, vaginascopes, and the like. For ease of description, however, an exemplary otoscope shall be described for the duration of this disclosure unless otherwise noted.

As shown in FIGS. 1 and 2, the medical diagnostic instrument 10 may include an instrument head 18 attached to the top of a handle 14. The handle 14 and/or the instrument head 18 may be substantially hollow, and the instrument head 18 may include a frustoconical tip portion 40 onto which a disposable speculum (not shown) may be fitted in a conventional manner. In an exemplary embodiment, the speculum may be sized, shaped, and/or otherwise configured to fit a predetermined distance into an ear canal of a patient so that, for example, the tympanic membrane or other medical target may be examined. The tip portion 40 may have an opening 42 at the distal end thereof, and an eye piece 46 may be attached to the proximal end 48 of the instrument head 18 to assist in such examination. Accordingly, in an exemplary embodiment, the eye piece 46 may form part of an optical path with the opening 42 through the hollow instrument head 18 to permit viewing of a medical target. While the tympanic membrane may be one such target, it is understood that other exemplary medical diagnostic instruments 10 may be utilized to view other like membranes or targets. Such exemplary medical targets may include portions of the eye, nose, throat, and/or other portions of the human anatomy.

Exemplary medical diagnostic instruments 10 may employ, for example, an incandescent lamp 22, such as, for example, a halogen or xenon lamp. At least a portion of such an incandescent lamp 22 may be mounted to, retained within, and/or otherwise associated with a housing 25 disposed within a base 27 or other portion of the instrument head 18. The incandescent lamp 22 may be functionally, electrically, and/or otherwise operably connected to a power supply within the medical diagnostic instrument 10 or to an external power supply. For example, the incandescent lamp 22 may be electrically connected to one or more batteries 26 retained in a compartment of the instrument handle 14. Alternatively, the instrument handle 14 and/or other portions of the medical diagnostic instrument 10 may be electrically connected to a conventional wall outlet or other similar power supply via an electrical cord (not shown) or other like connection. It is also understood that the medical diagnostic instrument 10 may employ one or more springs 33, pins 31, controls 30, and/or other components to assist in maintaining an effective electrical connection between the incandescent lamp 22 and the power supplies discussed above. Such components may also assist in controlling, for example, the current and/or voltage supplied to the incandescent lamp 22.

In an exemplary embodiment in which the medical diagnostic instrument 10 comprises an otoscope, the instrument 10 may also include a bundle of optical fibers 38 extending from proximate the incandescent lamp 22, through the base 27 of the instrument head 18, to a bundle of light transmitting ends 36 or other optical means that are disposed at the distal opening 42. The optical fibers 38 and the transmitting ends 36 may be configured to illuminate the medical target during examination.

Alternatively, in an exemplary embodiment in which the medical diagnostic instrument 10 comprises an ophthalmoscope, the bundle of optical fibers 38 may be omitted. Instead, in such an exemplary embodiment, the medical diagnostic instrument 10 may further comprise one or more collimating lenses, reticles, positive lenses, negative lenses, mirrors, and/or other optical or beam shaping components to direct radiation emitted by the incandescent lamp 22. For example, an exemplary ophthalmoscope may include a mirror that is offset from, for example, a central or optical axis of the incandescent lamp 22. Such a mirror may be configured to direct radiation emitted by the incandescent lamp 22 in the direction of the medical target optically downstream of, for example, a reticle of the ophthalmoscope. Such mirror positioning may be required due to, for example, the configuration of the ophthalmoscope head 18. To compensate for such off-axis or offset mirror positioning, the exemplary ophthalmoscope may further employ one or more prisms, wedges, and/or angled optical components optically downstream of the incandescent lamp 22 to direct light and/or other radiation emitted by the incandescent lamp 22 in the direction of the offset mirror.

In still another exemplary embodiment in which the medical diagnostic instrument 10 comprises an ophthalmoscope, the offset mirror described above may, instead, be substantially aligned with, for example, the central or optical axis of the incandescent lamp 22. In such an exemplary embodiment, one or more of the optical components described above for shifting and/or angling light emitted by the incandescent lamp 22 in the direction of the mirror may not be required.

FIGS. 8 through 11 illustrate an exemplary light assembly 8 of the present disclosure in which the incandescent lamp 22 has been replaced by a different light source such as, for example, an LED. Such an exemplary light source 12 is illustrated in greater detail in FIG. 12, and the light source 12 may comprise an LED, a low-intensity laser, and/or any other light source known in the art. For ease of description, however, an exemplary embodiment in which the light source 12 comprises an LED shall be described for the duration of this disclosure unless otherwise noted.

The incandescent lamp 22 discussed above can be replaced with one or more LEDs to illuminate a medical target during examination. Replacing an incandescent lamp 22 with an LED in this way may improve, for example, the durability, illumination, and/or other qualities of the instrument 10, and thus may be desirable in modern hand-held medical diagnostic instruments 10. In replacing an incandescent lamp 22 with an LED, one or more lenses or other additional optical components may be employed to shape the light emitted by the LED. Such components may bend, shift, collimate, focus, and/or otherwise shape the radiation emitted by the LED to substantially match the optical characteristics of the incandescent lamp 22 such that the functionality of the medical diagnostic instrument 10 may remain substantially unchanged.

In an exemplary embodiment, the light assembly 8 may include a light source 12 mounted to a substrate 16, and a circuit board 44 disposed inclined to the substrate 16. The assembly 8 may also include first and second connectors 54 mounting and electrically connecting the circuit board 44 to the substrate 16. Such an exemplary light assembly 8 may further include one or more heat sinks, and a thermal conductor 56 thermally connecting at least one of the heat sinks to the substrate 16.

In an exemplary embodiment, the substrate 16 may be constructed from plastics, polymers, and/or other typical circuit board material, and may comprise a printed circuit board. For example, the substrate 16 may include one or more electrical terminals embedded therein and/or otherwise formed thereon. Exemplary electrical terminals 32, 34 may be positive and negative electrical terminals, respectively. Such electrical terminals 32, 34 may be electrically and/or otherwise operably connected to one or more components disposed on the substrate 16. For example, the electrical terminals 32, 34 may be configured to provide and/or otherwise direct an electrical current and/or voltage from a power source, such as the batteries 26 of the medical diagnostic instrument 10, to the light source 12 mounted on the substrate 16. As shown in at least FIGS. 9 and 11, the substrate 16 may have a top surface 20 and a bottom surface 24. In an exemplary embodiment, the light source 12 may be disposed on and/or otherwise mounted to the top surface 20, and the bottom surface 24 may define and/or otherwise include the electrical terminals 32, 34 discussed above.

Figure 12:
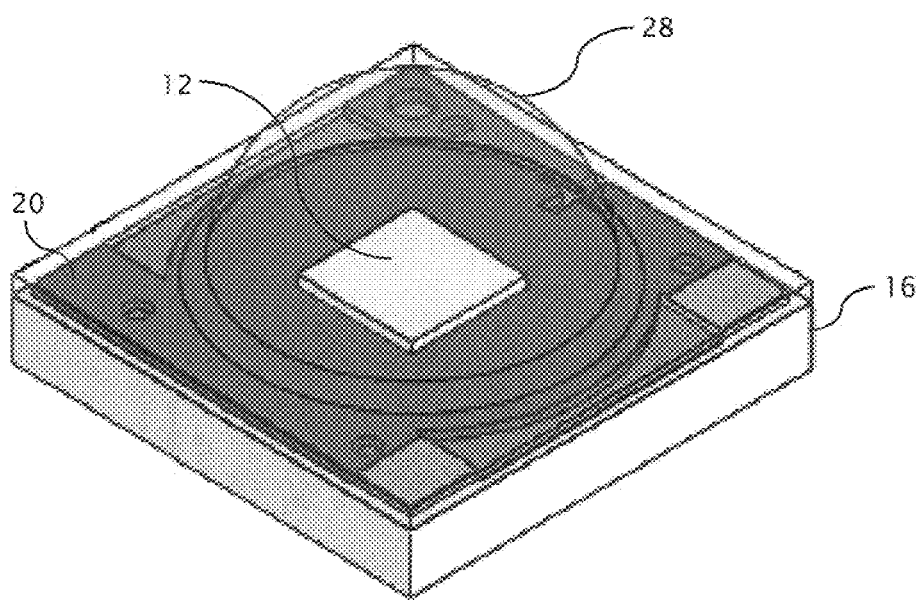
FIG. 12 is an isometric view of a light source and a substrate according to an exemplary embodiment of the present disclosure.

As shown in greater detail in FIG. 12, a cover 28 may be mounted on and/or otherwise connected to the substrate 16. The cover 28 may be, for example, substantially transparent to permit light and/or other radiation emitted by the light source 12 to pass through the cover 28 to a lens 62 of the light assembly 8. The cover 28 may have any shape, size, and/or other configuration known in the art. For example, the cover 28 may be substantially convex, and may act as a positive lens. In such an exemplary embodiment, the cover 28 may assist in collecting and/or otherwise focusing divergent light emitted by the light source 12. Alternatively, the cover 28 may be substantially planar, thereby providing substantially no added intensification of the emitted light. In still another exemplary embodiment, at least a portion of the cover 28 may be substantially concave, and may act as a negative lens. In such an embodiment, the concave portion of the cover 28 may act as a negative lens and may assist in further diverging the light emitted by the light source 12. The light emitted by the light source 12 may pass through an air gap 29 between the cover 28 and the lens 62 before reaching the lens 62.

The lens 62 may have any shape, size, and/or other configuration known in the art to assist in bending, shifting, angling, shaping, focusing collimating, and/or diverging the light emitted by the light source 12 optically upstream of the other optical components of the medical diagnostic instrument 10. For example, the lens 62 may be shaped, sized, and/or otherwise configured to modify the path, orientation, intensity, and/or other optical characteristics of the light emitted by the light source 12 to substantially match the corresponding optical characteristics of the radiation emitted by an incandescent lamp 22 previously employed by the medical diagnostic instrument 10. Thus, the combination of the lens 62 and light source 12 may be utilized as a direct replacement for incandescent lamps 22 commonly used in otoscopes, ophthalmoscopes, vaginascopes, and other known hand-held medical diagnostic instruments 10. Due to the configurations of the light source 10 and the lens 62, these components may replace such incandescent lamps 22 without further modifications to, for example, the light assembly 8 or other hand-held medical diagnostic instrument components.

The lens 62 may be fixed relative to the light source 12 in order to maintain the desired beam-shaping effect on the light emitted by the light source 12. In an exemplary embodiment, the lens 62 may be mounted on and/or otherwise connected to the substrate 16 by any known means. For example, an adhesive 15 may be disposed between, for example, one or more mounting surfaces 84 of the lens 62 and the top surface 20 of the substrate 16. Alternatively, at least a portion of the lens 62 may be molded onto the substrate 16. In still a further exemplary embodiment, the lens 62 may define one or more grooves, clips, slots, notches, shoulders, and/or other known retention components to assist in fixedly disposing the substrate 16 relative to the lens 62.

Figure 3:
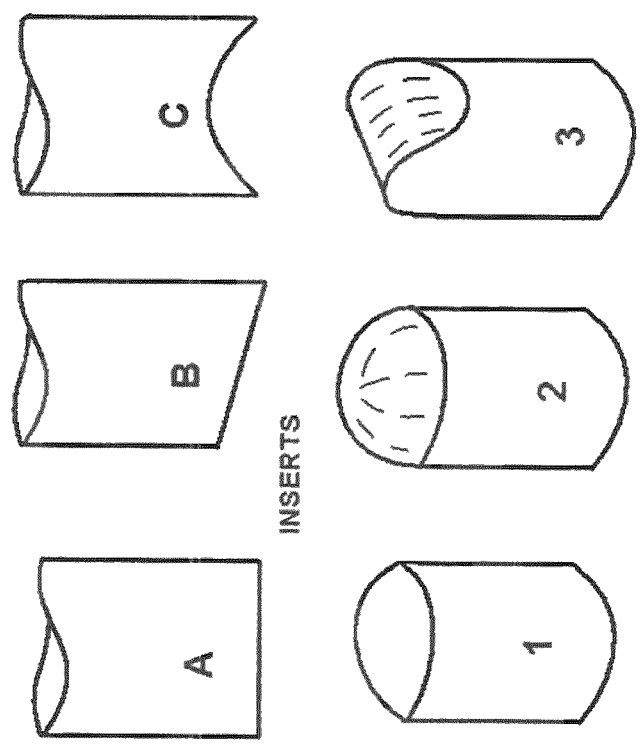
FIG. 3 illustrates a lens mold and a plurality of inserts according to an exemplary embodiment of the present disclosure.
Figure 3:
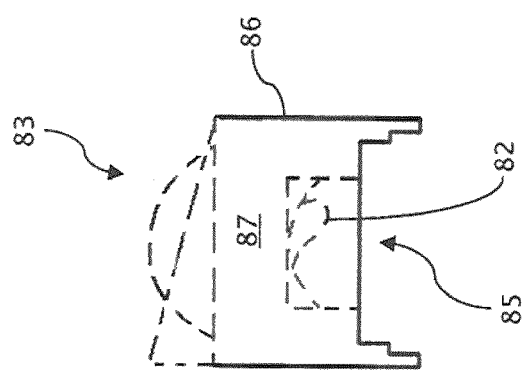

As shown in, FIGS. 3-7, the lens 62 may have any number of configurations in order to desirably shape a beam or other radiation emitted by the light source 12. For example, the shape, size, and/or other configurations of the lens 62 may be designed to desirably shape the light emitted by the light source 12 to match one or more different filament configurations of an incandescent lamp 22 previously utilized in known hand-held medical diagnostic instruments 10. Such lenses 62 may be formed by any known lens-formation process including, for example, casting, molding, and/or other processes. For example, the lenses 62 of the present disclosure may be formed through a known blown or injection molding process in which a universal mold 86 is utilized to form lenses 62 having a variety of different configurations. As shown in FIG. 3, a plurality of different inserts may be utilized in conjunction with the mold 86 to form lenses 62 having different configurations and, thus, different optical characteristics. As indicated in FIG. 3, any of Inserts A, B, C may be inserted into a first portion or end 83 of the mold 86 while any of Inserts 1, 2, 3 may be inserted into a second portion or end 85 of the mold 86. In still further exemplary embodiments, the Inserts A, B, C, 1, 2, 3 may be interchangeable. In such embodiments, any of the Inserts may be inserted into and used in the first end 83 and/or the second end 85 of the mold 86. A cavity 87 of the mold 86 between the first and second ends 83, 85 may then be filled with a flow of lens material to form lenses 62 having various characteristics. For example, optical surfaces 89 of the Inserts A, B, C, 1, 2, 3 may form corresponding optical surfaces on the resulting lenses 62. In an exemplary embodiment, the optical surfaces of the lenses 62 may be any of the concave surfaces 74, planar surfaces 76, 78, convex surfaces 80, saddle-shaped surfaces 82, or other lens surfaces discussed herein.

Figure 6:
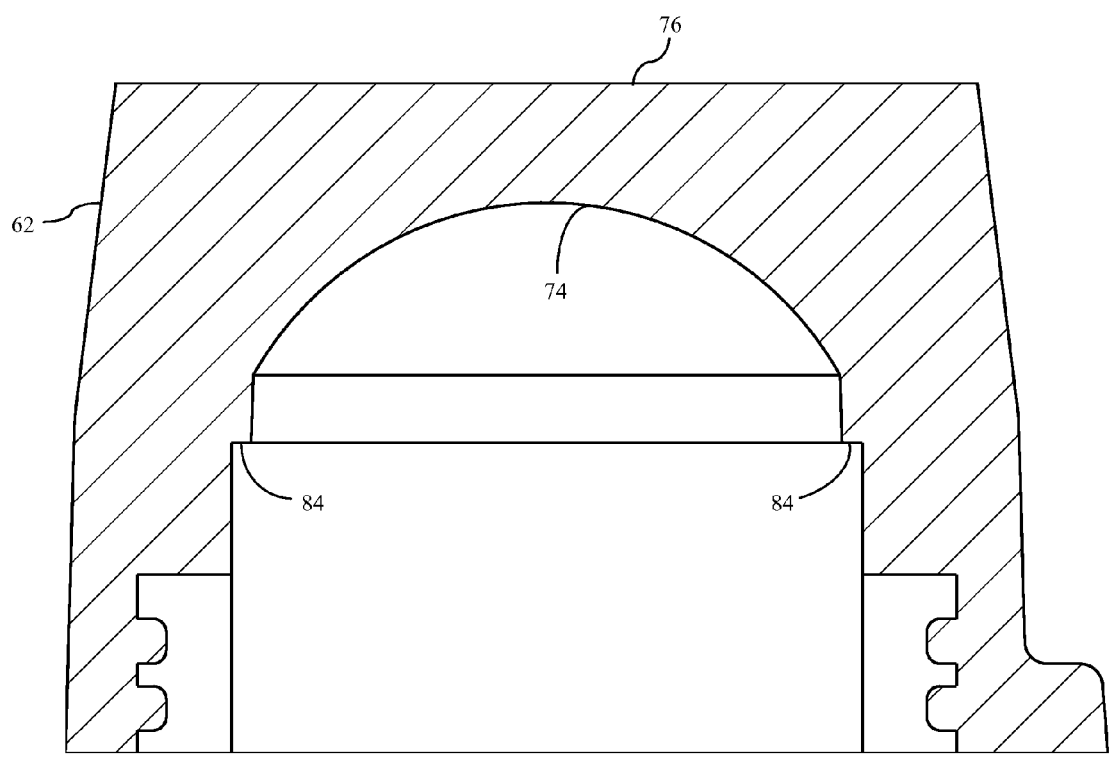
FIG. 6 is a cross-sectional view of a lens according to still another exemplary embodiment of the present disclosure.

For example, in an embodiment in which the medical diagnostic instrument 10 comprises an ophthalmoscope, magnification of the light emitted by the light source 12 may not be required. In such an exemplary embodiment, a lens 62 having a substantially planar top optical surface 76 and a substantially concave light-receiving optical surface 74 may be utilized. In order to form such a lens 62, Insert 2 may be inserted into the second end 85 of the mold 86 and Insert A may be inserted into the first end 83 of the mold 86. A lens 62 formed using Insert 2A is illustrated in FIG. 6.

Figure 7:
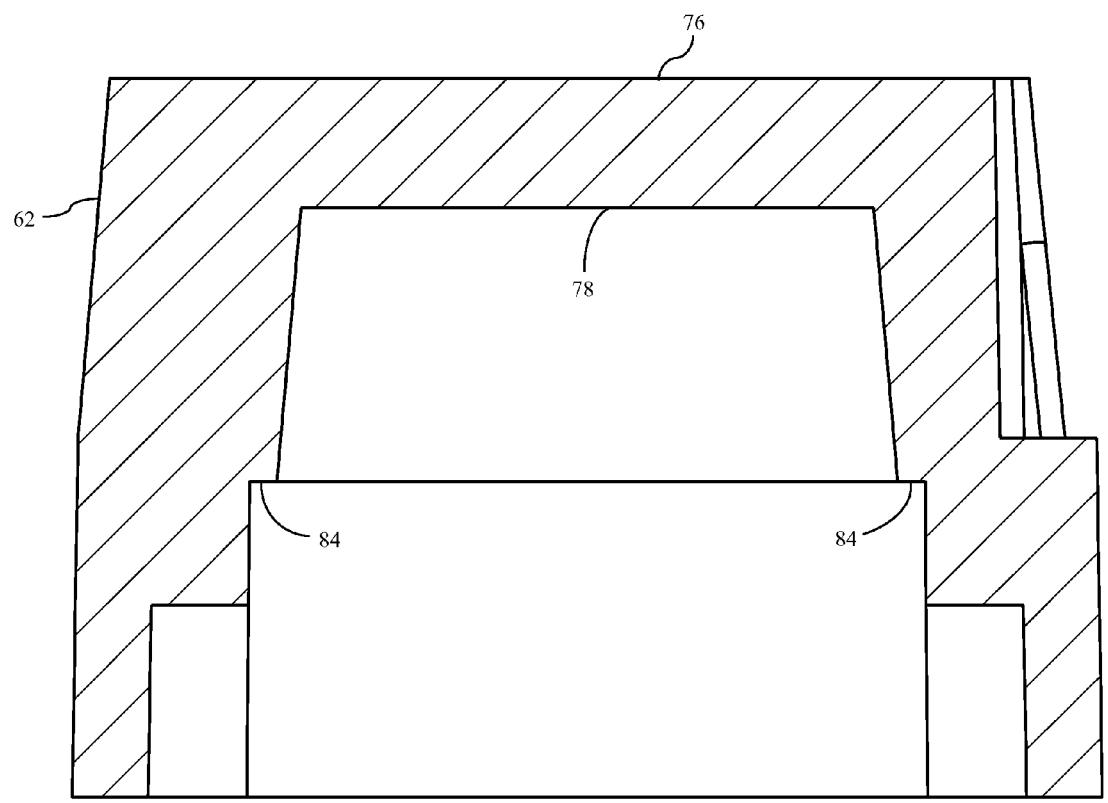
FIG. 7 is a cross-sectional view of a lens according to a further exemplary embodiment of the present disclosure.

In another exemplary ophthalmoscope embodiment, Insert 2 may be replaced with Insert 1 in the second end 85 of the mold 86 to form a lens 62 having a substantially planar light-receiving optical surface 78. Such an exemplary lens 62 is shown in FIG. 7. The planar optical surface 78 may provide substantially no magnification to the light emitted by the light source 12, while the concave light-receiving optical surface 74 may cause further diffraction of such light. Accordingly, the concave surface 74 may act as a negative lens reducing the power and/or intensity of the light produced by the light source 12.

Figure 5:
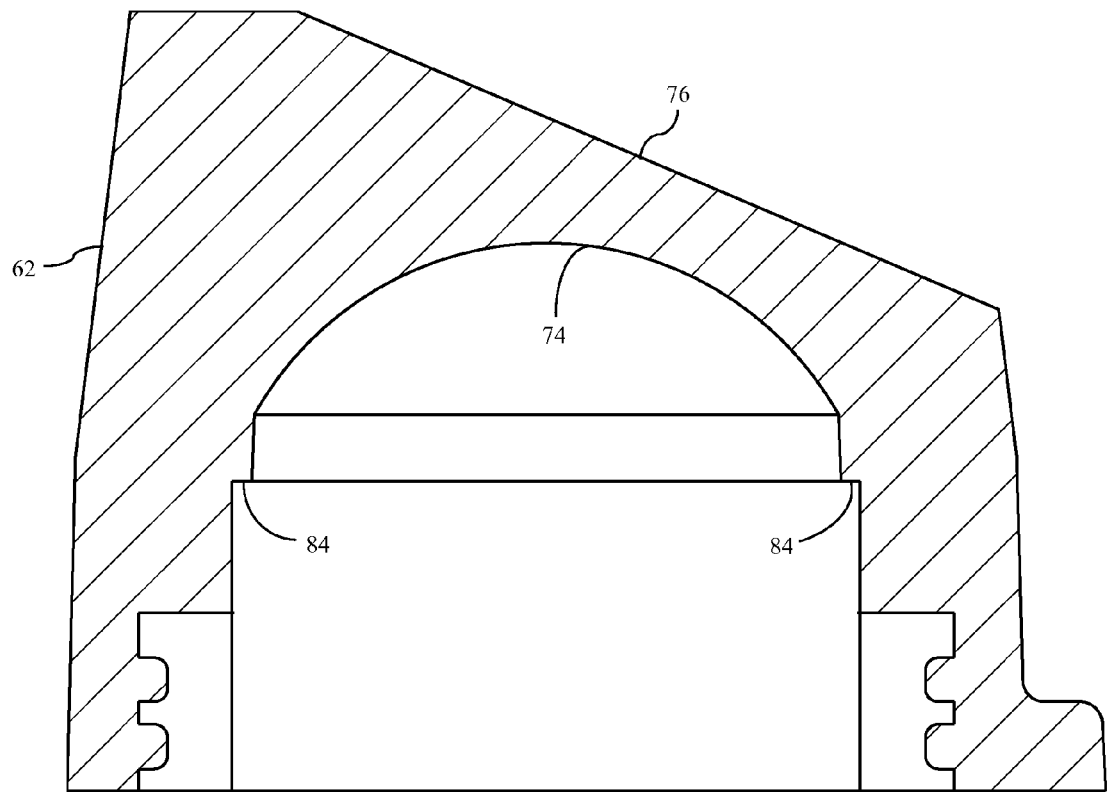
FIG. 5 is a cross-sectional view of a lens according to another exemplary embodiment of the present disclosure.

In additional exemplary ophthalmoscope embodiments, there may be a need to skew and/or otherwise direct light emitted by the light source 12 at an angle relative to, for example, an optical axis 90 (FIGS. 9 and 11) of the light source 12. In such exemplary embodiments, the ophthalmoscope may employ one or more mirrors, lenses, and/or other optical components to receive such skewed and/or angled light, and redirect such light toward the medical target. In order to angle or skew the light emitted by the light source 12, the planar optical surface 76 of the lens 62 may be formed of any desirable angle relative to, for example, the horizontal or to one or more mounting surfaces 84 defined by the lens 62. Such an exemplary lens 62 is shown in FIG. 5, whereby the planar optical surface 76 is inclined relative to the mounting surface 84. The lens 62 illustrated in FIG. 5 may correspond to a lens formed using Insert 2 disposed in the second end 85 of the mold 86, and the Insert B disposed in the first end 83 of the mold 86 (FIG. 3). In further exemplary embodiments, either of Inserts 1 or 3 may be substituted for Insert 2 in the second end 85 of the mold 86 to form a lens 62 capable of angling or skewing emitted by the light source 12. It is understood that utilizing Insert 1 may form a lens 62 having a planar optical surface 78 having substantially no magnification effect on the light received thereby, while light received by a substantially saddle-shaped optical surface 82 (shown as a dashed line in FIG. 3) of a lens 62 formed by the Insert 3 may be spread, stretched, and/or otherwise dispersed in any desired direction depending on the optical requirements of the ophthalmoscope.

Figure 4:
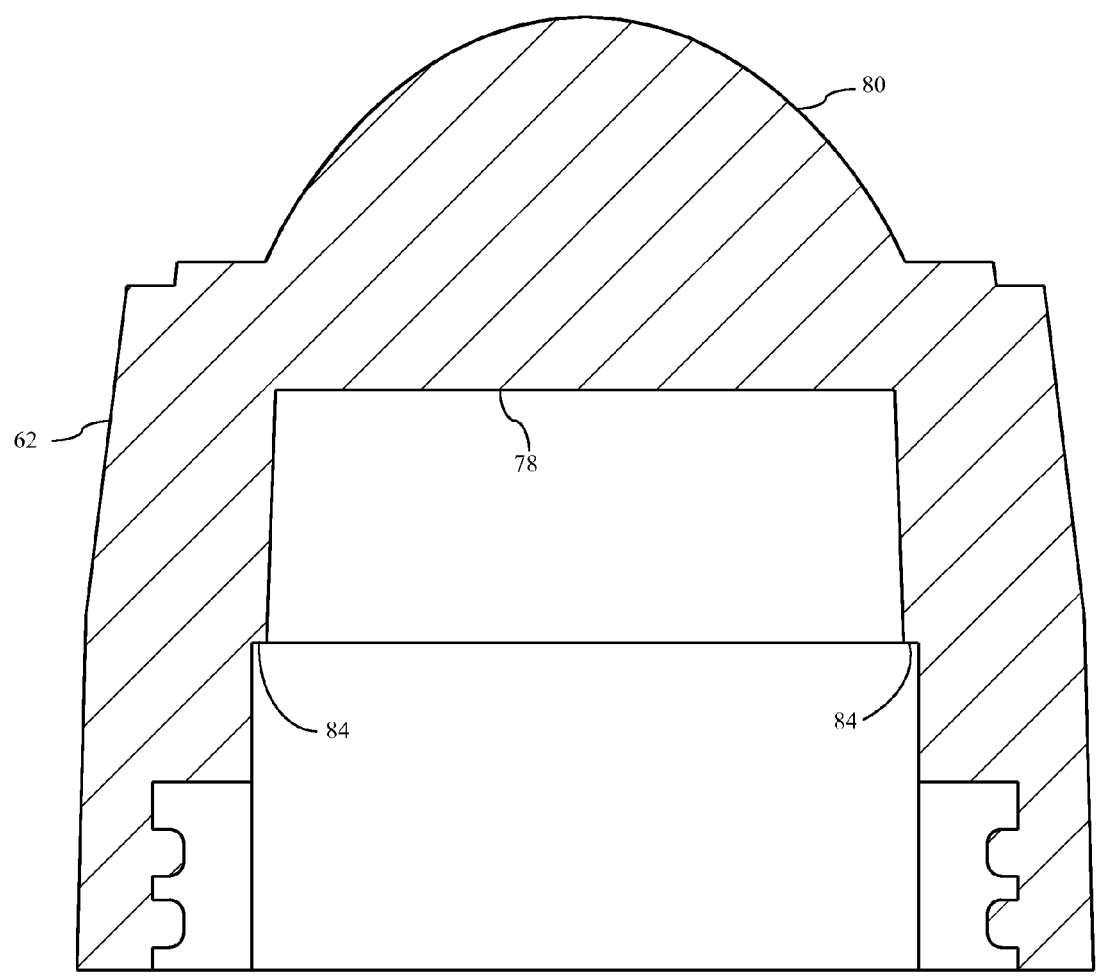
FIG. 4 is a cross-sectional view of a lens according to an exemplary embodiment of the present disclosure.

Alternatively, in an exemplary embodiment in which the medical diagnostic instrument 10 comprises an otoscope, as in FIGS. 1 and 2, the lens 62 may be sized, shaped, and/or otherwise configured to direct light emitted by the light source 12 onto optical fibers 38. In an exemplary embodiment, the lens 62 may be configured to focus the light emitted by the light source 12 onto the fibers 38, thereby increasing the intensity and/or power of the light. In such an exemplary embodiment, the Insert 1 may be inserted into the second end 85 of the mold 86 and the Insert C may be inserted into the first end 83 of the mold 86. A lens 62 formed using such inserts is shown in FIG. 4. As shown in FIG. 4, such a configuration may form a lens 62 having a substantially planar optical surface 78 configured to receive the light emitted by the light source 12, and a convex optical surface 80 configured to focus the light passing therethrough.

One of ordinary skill in the art will appreciate that employing a universal mold 86 and a variety of easily removable, insertable, and interchangeable Inserts 1, 2, 3, A, B, C may assist in streamlining the lens formation process. In particular, using a universal mold 86 and Inserts 1, 2, 3, A, B, C may reduce the amount of time required for lens formation and may require far less tooling than known injection or blown molding processes, thereby reducing the expense involved in forming lenses 62 of the type described herein.

As shown in FIGS. 8 through 11, the lens 62 may be mounted on and/or otherwise supported by a shoulder 64 defined by the housing 25. In an exemplary embodiment, the shoulder 64 may be etched, milled, and/or otherwise formed in a sidewall or inner wall of the housing 25. The shoulder 64 may be formed at a distance d from a distal end 88 of the housing 25 so as to dispose the lens 62 and/or the light source 12 connected to the lens 62 at a desired position relative to the housing 25. For example, the size, shape, depth, position, and/or other configurations of the shoulder 64 may assist in positioning the lens 62 and/or the light source 12 at a desired position along a longitudinal axis 60 of the housing 25. Such positioning of, for example, the light source 12 may streamline the assembly process of the light assembly 8 and may also assist in standardizing the optical characteristics of the assembled light assembly 8 in a process in which the light assemblies 8 are mass-produced. For example, in exemplary embodiments in which the instrument 10 comprises an ophthalmoscope, the shoulder 64 may assist in disposing the light source 12 at a desired distance d from the distal end 88, thereby enabling the lens 62 to accurately and repeatably focus light emitted by the light source 12 onto, for example, collimating lenses, reticles, positive lenses, mirrors, and/or other optical components at a fixed position optically downstream of the light source 12 within the instrument 10. In such an exemplary embodiment, disposing, for example, the light source 12 and/or the lens 62 accurately along the longitudinal axis 60 may be required for optimal performance of the instrument 10.

To further assist in positioning and/or aligning the lens 62 and/or the light source 12 relative to the housing 25, the housing 25 may also define one or more keyways 66 proximate the distal end 88. The keyway 66 may be formed within a sidewall and/or inner wall of the housing 25 through any of the processes discussed above with regard to the shoulder 64. In an exemplary embodiment, the keyway 66 may be a channel extending substantially parallel to the longitudinal axis 60 of the housing 25, and the keyway 66 may be configured to mate with and/or otherwise accept a corresponding key 68 of the lens 62. In an exemplary embodiment, the key 68 may be inserted into the keyway 66 for radial alignment of the lens 62 and/or the light source 12 about the longitudinal axis 60 of the housing 25.

Such radial alignment of the light source 12 and/or lens 62 clockwise or counter-clockwise about the axis 60 may be useful in exemplary embodiments in which the instrument 10 comprises an ophthalmoscope or other instrument comprising optical components configured to accept stretched, flattened, shifted, angled, and/or otherwise modified beams of light from the light source 12. Such optical components may be configured to receive modified light beams from various filaments employed by incandescent lamps 22. Accordingly, aligning the lens 62 and/or light source 12 utilizing, for example, the keyway 66 and key 68 arrangement described above may assist in easily replacing such lamps 22 while satisfying the optical requirements of the particular instrument 10.

To further assist in desirably aligning the light source 12, lens 62, and/or housing 25, the housing 25 may be equipped with one or more pins 72 disposed on an outer wall 70 of the housing 25. In an exemplary embodiment, the pin 72 may be made from substantially the same material as the housing 25, and the pin 72 may be spot welded, press fit, adhered, and/or otherwise connected to the housing 25. Alternatively, the pin 72 may be milled and/or otherwise machined from the outer wall 70 of the housing 25 such that the housing 25 and the pin 72 are formed from the same piece of material. The pin 72 may be disposed at a distance D from the distal end 88 of the housing 25 in order to assist in positioning the light assembly 8 at a desired depth or location within the base 27 of the instrument 10. For example, the base 27 may define one or more channels (not shown) configured to accept the pin 72, and such channels may be configured to position the light assembly 8 at a desired depth or longitudinal location within the base 27. Such a longitudinal location may dispose, for example, the light source 12 a desired depth or longitudinal distance away from one or more optical components of the instrument 10. In addition, the pin 72 may be aligned with the keyway 66, key 68, and/or the light source 12. In an exemplary embodiment, the pin 72 may be disposed on the outer wall 70 coplanar with the longitudinal axis 60 of the housing 25 and the keyway 66. Aligning the pin 72 in this way may assist in radially aligning, for example, the light source 12, lens 62, and/or housing 25 relative to the base 27 and/or to the downstream optical components of the instrument 10. As described above, such radial alignment may assist in satisfying the optical requirements of such optical components, and may facilitate easy replacement of an incandescent lamp 22 with the light assembly 8 of the present disclosure.

In addition, the location and/or other configurations of the keyway 66 may enable the pin 72 to be connected to and/or formed on the housing 25 prior to mounting, for example, the lens 62 and/or the light source 12 within the housing 25. Disposing the pin 72 at a distance D from the distal end 88, and coplanar with the axis 60 and the keyway 66 may eliminate the need for optical alignment of the light source 12 and/or lens 62 relative to the housing 25, and may also eliminate the need for separate pinning of the housing 25 after such optical alignment is completed. Eliminating these steps may simplify assembly, and reduce the cost and time required for manufacturing the light assembly 8.

As shown in FIGS. 8 through 11, the light assembly 8 may further include a circuit board 44 defining one or more terminals 50, 52. In an exemplary embodiment, the circuit board 44 may be a conventional printed circuit board including one or more drive, voltage control, current control, and/or other control components of the light assembly 8. The circuit board 44 may be any shape, size, and/or other configuration to permit convenient disposal and/or mounting within, for example, a chamber 58 of the housing 25. For example, the circuit board 44 may be substantially rectangular in shape, and may have a width less than a width and/or diameter of the chamber 58. The circuit board 44 may also have a length less than a length of the chamber 58 to facilitate disposal of the circuit board 44 within the chamber 58.

In an exemplary embodiment, the circuit board 44 may extend substantially parallel to an optical axis 90 of the light source 12. The optical axis 90 may be parallel to and/or collinear with the longitudinal axis 60 of the housing 25. Alternatively, the optical axis 90 may be parallel to and offset from the axis 60. Although FIG. 9 illustrates the circuit board 44 being disposed substantially parallel to the optical axis 90, in additional exemplary embodiments, the circuit board 44 may be disposed at any desired angle relative to the optical axis 90 to facilitate connecting the circuit board 44 to the substrate 16 and/or mounting the circuit board 44 within the chamber 58.

The circuit board 44 may be mechanically and/or electrically connected to the substrate 16 in any conventional way. For example, one or more clips, pins, teeth, grooves, and/or other known connection devices may be employed to facilitate a mechanical connection between the substrate 16 and the circuit board 44. Likewise, one or more leads, wires, solder beads, and/or other electrical connectors may be employed to form one or more electrical connections between the substrate 16 and the circuit board 44, and/or between components of the substrate 16 and respective components of the circuit board 44. In an exemplary embodiment, at least one of the connection devices discussed above may form both a mechanical connection and an electrical connection between the substrate 16 and the circuit board 44, and/or between respective components of the substrate 16 and the circuit board 44.

Figure 8:
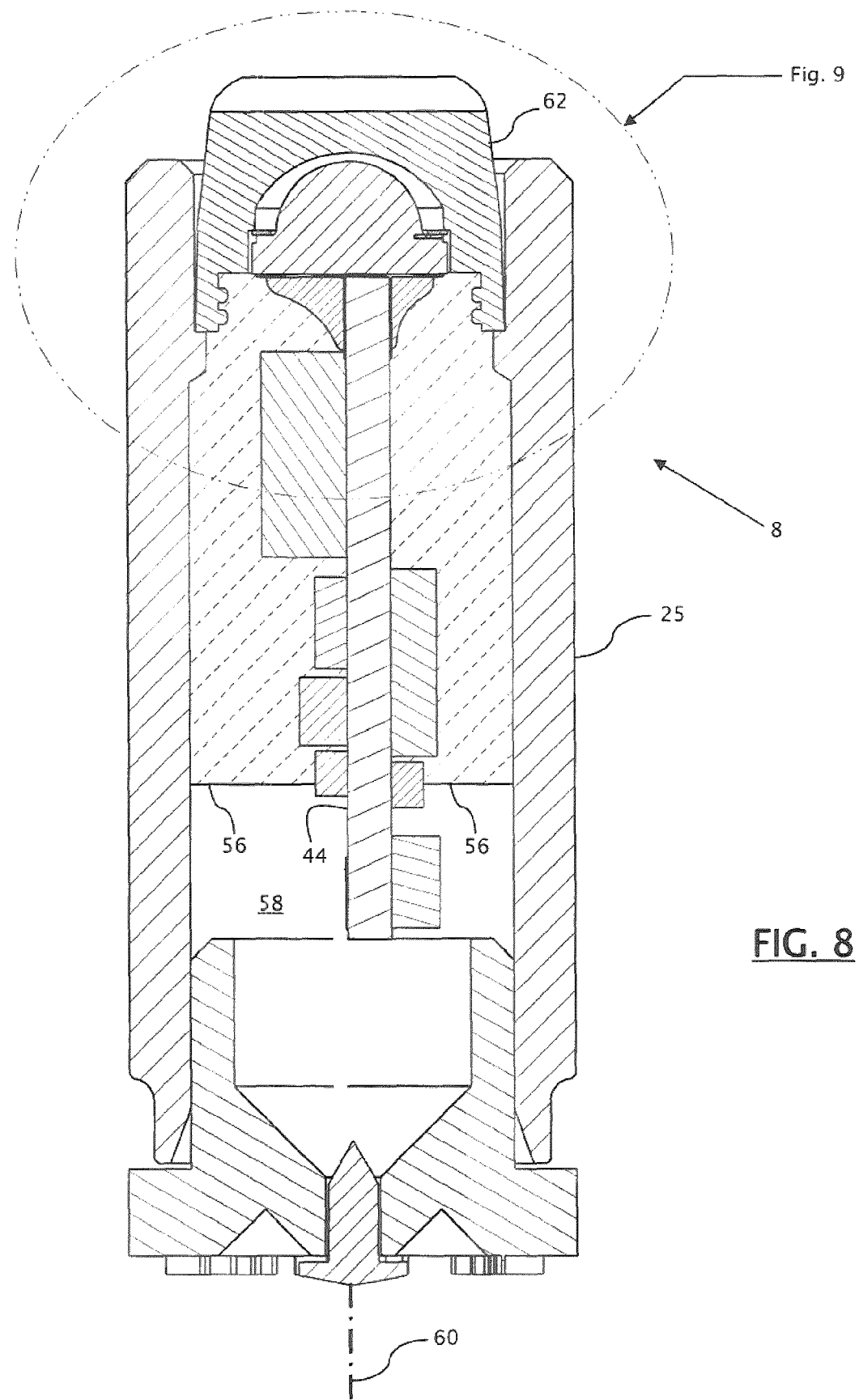
FIG. 8 is a cross-sectional view of a replacement light assembly according to an exemplary embodiment of the present disclosure.
Figure 9:
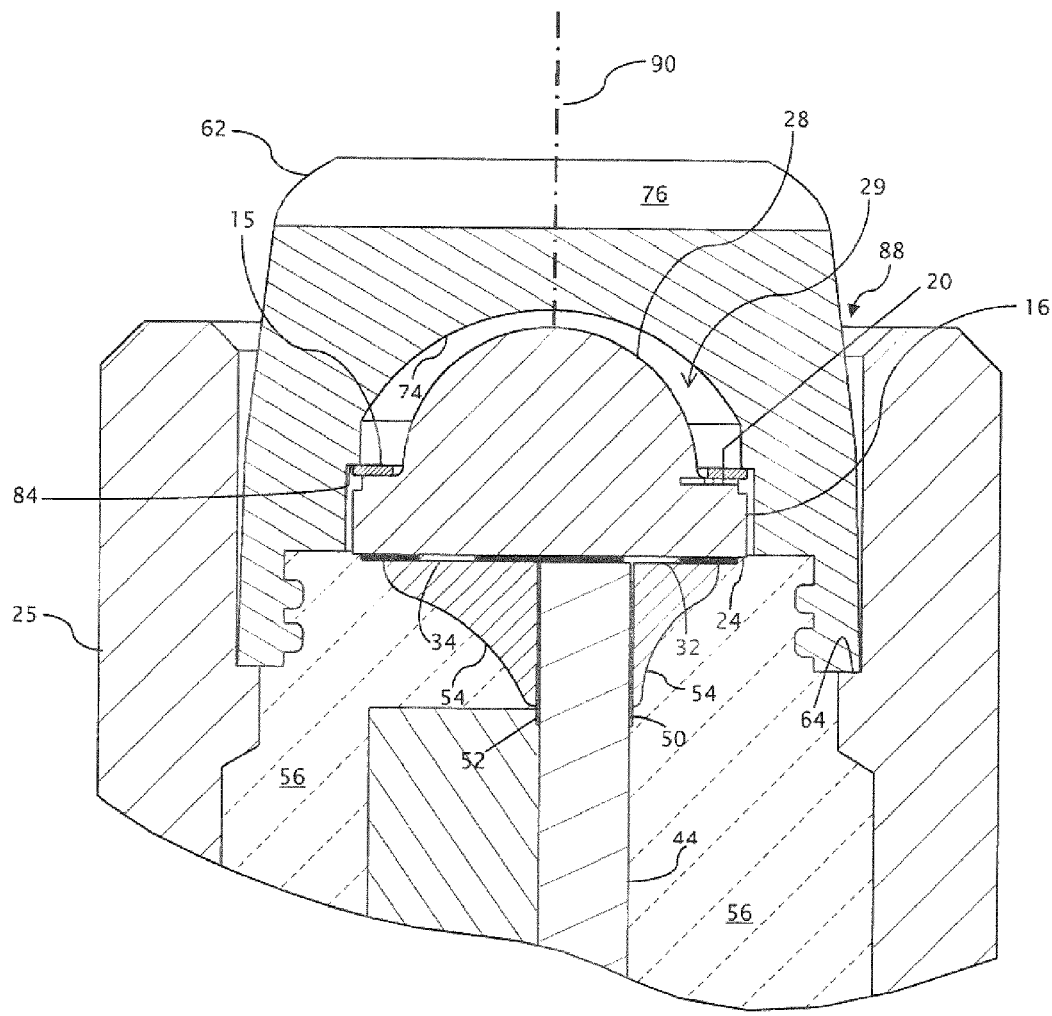
FIG. 9 is an enlarged view of a portion of the assembly illustrated in FIG. 8.

For example, as illustrated in FIGS. 8 and 9, one or more connectors 54 may be disposed between the substrate 16 and the circuit board 44 to form both an electrical connection and a mechanical connection therebetween. In an exemplary embodiment, the connectors 54 may comprise one or more beads of solder mounting and electrically connecting at least a portion of the substrate 16 to a corresponding portion of the circuit board 44. In an exemplary embodiment, the connectors 54 may mount and electrically connect the first terminal 32 of the substrate 16 to the first terminal 50 of the circuit board 44. In such an exemplary embodiment, a second connector 54 may also mount and electrically connect the second terminal 34 of the substrate 16 to the second terminal 52 of the circuit board 44. In such an exemplary embodiment, the connectors 54 may extend along at least a portion of the width of the circuit board 44. Alternatively, the connectors 54 may be disposed substantially locally, so as to form isolated areas of connection between corresponding terminals of the substrate 15 and circuit board 44. Accordingly, the size, location, and/or other configurations of the connectors 54 may substantially correspond to the corresponding configurations of the terminals 32, 34, 50, 52 described above.

In addition to mounting and/or electrically connecting the substrate 16 to the circuit board 44, the substrate 16 may also be thermally connected to the circuit board 44. In an exemplary embodiment, the electrical terminals 32, 34 of the substrate 16 may be thermally connected to the corresponding electrical terminals 50, 52 of the circuit board 44 during assembly, and such a thermal connection may be formed by, for example, one or more of the connectors 54 discussed above. For example, one or more of the connectors 54 may form an electrical, mechanical, and thermal connection between the substrate 16 and the circuit board 44 at the respective terminals thereof. Such a thermal connection may be useful in removing and/or dissipating heat from portions of the substrate 16 and/or portions of the circuit board 44.

For example, the connectors 54 may be employed to remove heat from the terminals 32, 34 of the substrate 16 and/or the terminals 50, 52 of the circuit board 44 by thermally connecting the connectors 54 to one or more active or passive cooling devices. Such cooling devices may be disposed within, for example, the chamber 58. Alternatively, such devices may be disposed external to the housing 25.

In still another exemplary embodiment, such cooling devices may be incorporated into the circuit board 44, housing 25, and/or other components of the light assembly 8 or the instrument 10. For example, such cooling devices may comprise one or more heat sinks mounted to the circuit board 44, housing 25, base 27, handle 14, or other components of the instrument 10. In still another exemplary embodiment, one or more components of the instrument 10 or the light assembly 8 may comprise a heat sink configured to draw and/or otherwise dissipate heat from the substrate 16 and/or the circuit board 44. For example, the housing 25 may comprise one or more fins or other passive cooling devices configured to assist in dissipating heat from the substrate 16 and/or the circuit board 44. In still a further exemplary embodiment, the housing 25 may comprise a heat sink, and at least a portion of the housing 25 may be thermally connected to at least one of the terminals 32, 34 of the substrate 16 and/or the terminals 50, 52 of the circuit board 44 to remove heat therefrom.

In an exemplary embodiment, a thermal connection may be formed between the terminals 32, 34, 50, 52 and the housing 25 via one or more of the connectors 54 discussed above. Such a thermal connection may be formed by any thermally conductive material or structure known in the art disposed between the terminals 32, 34, 50, 52 and the housing 25. For example, as shown in FIGS. 8 through 11, a thermal conductor 56 may be disposed within the chamber 58 thermally connecting at least one of the terminals 32, 34, 50, 52 to the housing 25 and/or any other heat sink of the light assembly 8. Such a thermal connection may be formed between the terminals and the heat sink via at least one of the connectors 54. The thermal conductor 56 may comprise an electrically insulative material such that the thermal conductor 56 may come in contact with one or more electrically conductive components of the light assembly 8 without causing the light assembly 8 to short-circuit. In addition, an electrically insulative thermal conductor 56 may be utilized to overlay portions of the substrate 16, circuit board 44, and/or components thereof, without causing damage to the light assembly 8.

In an exemplary embodiment, the thermal conductor 56 may comprise a thermally conductive epoxy overlaying at least a portion of the circuit board 44, as well as the connectors 54. Accordingly, the thermal conductor 56 may thermally connect the circuit board 44, substrate 16, terminals 32, 34, 50, 52, and/or connectors 54 to the housing 25 and/or one or more of the heat sinks discussed above.

Figure 10:
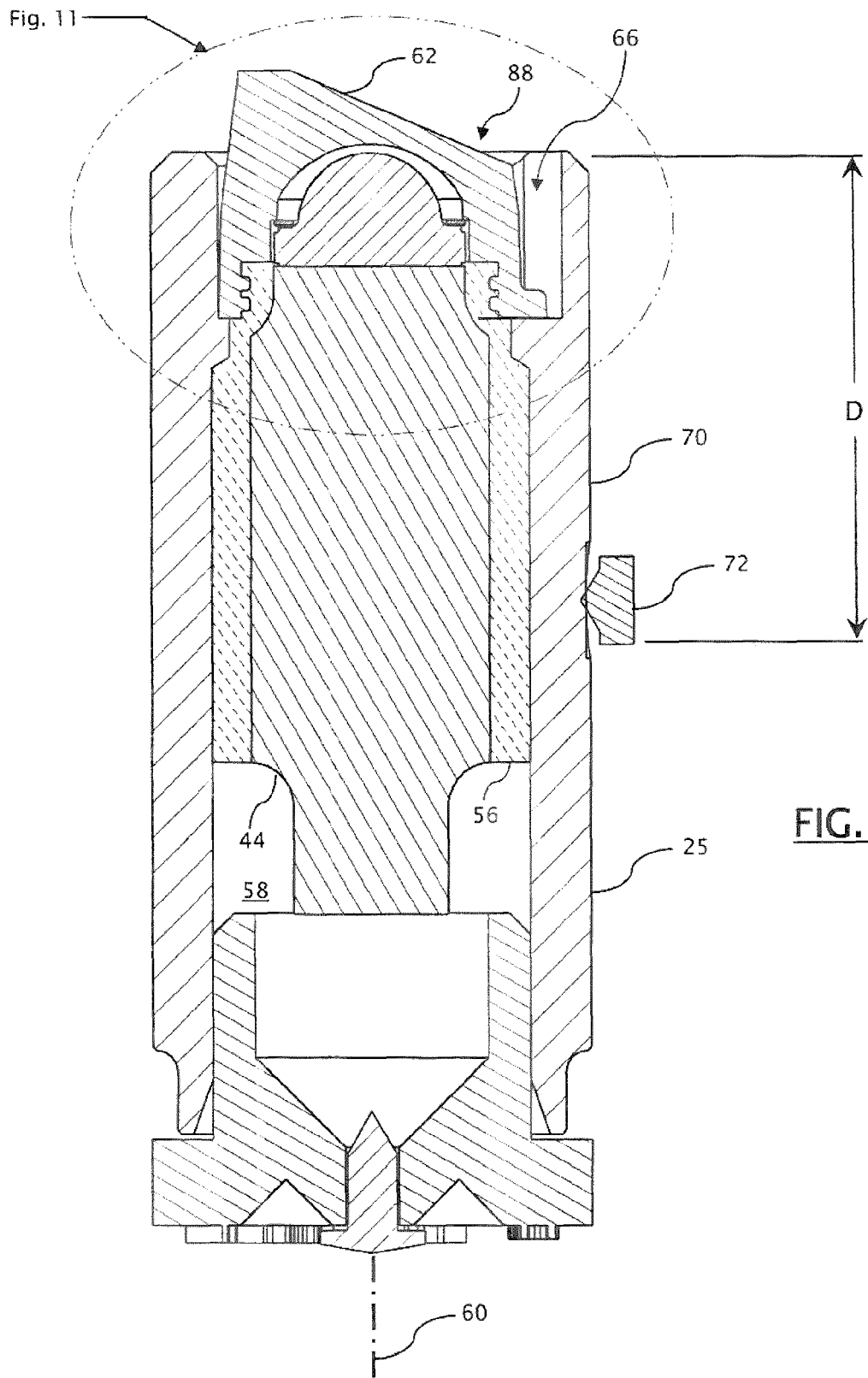
FIG. 10 is another cross-sectional view of the assembly shown in FIG. 8.
Figure 11:
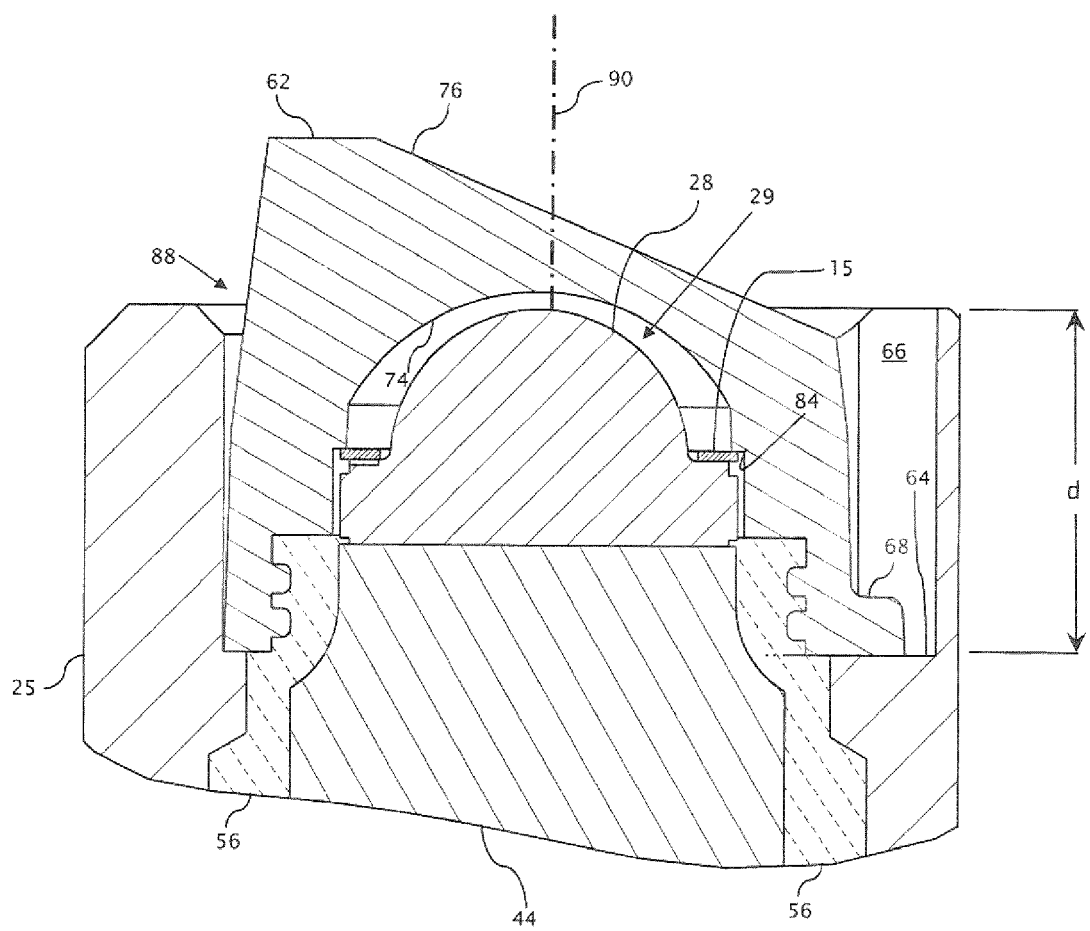
FIG. 11 is an enlarged view of a portion of the assembly shown in FIG. 10.

As shown in FIGS. 8 through 10, the thermal conductor 56 may substantially fill at least a portion of the chamber 58 around the circuit board 44. In such an exemplary embodiment, the circuit board 44 and/or the substrate 16 may be substantially submerged within the thermal conductor 56. The thermal conductor 56 may remain substantially gelatinous or may be configured to stiffen and/or harden, thereby assisting in supporting the circuit board 44 and/or the substrate 16 within the chamber 58. In an exemplary embodiment, the thermal conductor 56 may adhere to, bond with, and/or otherwise remain substantially fixed to the housing 25, circuit board 44, and/or substrate 16 to assist in securing the substrate 16 and/or the circuit board 44 relative to, for example, the housing 25.

In an exemplary embodiment, the housing 25 may be mechanically and/or thermally connected to the base 27 and/or the head 18. In addition, the base 27 and/or the head 18 may be mechanically and/or thermally connected to the handle 14 of the instrument 10. In such exemplary embodiments, each of these thermal connections may further assist in drawing heat from and/or dissipating heat from, for example, the terminals 32, 34, 50, 52.

In such an exemplary embodiment, each of the housing 25, base 27, head 18, and handle 14 may act as a heat sink assisting in passively cooling the terminals 32, 34, 50, 52. It is understood that by cooling one or more of the terminals described above, one or more components connected to the substrate 16 and/or the circuit board 44 may also be cooled. For example, dissipating heat from the terminals 32, 34 of the substrate 16 may assist in cooling the light source 12 disposed on the substrate 16. In an exemplary embodiment in which the light source 12 comprises an LED, such cooling may be useful in maintaining a satisfactory LED operating temperature. For example, embodiments of such LEDs may have an optimal operating temperature above which the efficiency, durability, and/or other operating characteristics of the LED may decrease to undesirable levels. Operating the LED above such temperatures may also cause damage to the LED.

In an exemplary embodiment, the junction temperature (a temperature measured at the junction between the LED and the substrate 16) may be monitored and/or regulated using one of the heat sinks or other cooling devices discussed above. Exemplary LEDs of the present disclosure may have a maximum junction temperature of approximately 85° C. In such an exemplary embodiment, the heat sinks, thermal conductor 56, connectors 54, and/or other components of the present disclosure may assist in maintaining the aforementioned junction temperature below approximately 85° C. by assisting in dissipating and/or drawing heat from the terminals 32, 34 of the substrate 16. It is also understood that additional passes and/or active cooling devices may be utilized with light assemblies 8 of the present disclosure in order to maintain and/or otherwise regulate the junction temperature or other thermal operating requirements of the light sources 12 discussed herein.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A light assembly for a hand-held medical diagnostic instrument, comprising:
   (a) a substrate having a top surface and a bottom surface, a light source mounted to the top surface, and the bottom surface having first and second electrical terminals;
   (b) a circuit board disposed inclined to the substrate, the circuit board having first and second electrical terminals;
   (c) a first connector mounting and electrically connecting the first electrical terminal of the substrate to the first electrical terminal of the circuit board;
   (d) a second connector mounting and electrically connecting the second electrical terminal of the substrate to the second electrical terminal of the circuit board;
   (e) a heat sink, wherein the heat sink comprises a thermally conductive housing extending about the circuit board; and
   (f) a thermal conductor thermally connecting at least one of the first and second electrical terminals of the substrate to the heat sink.

2. The assembly of claim 1, the thermal conductor thermally connecting the at least one electrical terminal to the heat sink via one of the first and second connectors.

3. The assembly of claim 1, wherein the thermal conductor comprises an electrically insulative material.

4. The assembly of claim 3, wherein the thermal conductor comprises an epoxy substantially overlaying the circuit board and the first and second connectors.

5. The assembly of claim 1, the thermal conductor thermally connecting the circuit board to the heat sink.

6. The assembly of claim 1, wherein the housing defines a chamber, the thermal conductor substantially filling the chamber around the circuit board.

7. The assembly of claim 1, wherein the housing defines a longitudinal axis and a shoulder substantially perpendicular to the longitudinal axis.

8. The assembly of claim 7, further including a lens overlaying the light source, the lens contacting the shoulder and directing radiation from the light source to a target.

9. The assembly of claim 8, wherein the lens is fixed relative to the light source such that contact between the shoulder and the lens disposes the light source at a desired position along the longitudinal axis.

10. The assembly of claim 1, wherein the housing defines a longitudinal axis and a keyway extending substantially parallel to the longitudinal axis.

11. The assembly of claim 10, further including a lens fixed relative to the light source and defining a key disposed within the keyway, the key fixing the light source at a desired radial position about the longitudinal axis.

12. The assembly of claim 10, the housing including a cylindrical outer wall, and a pin disposed on the outer wall coplanar with the longitudinal axis and the keyway.

13. The assembly of claim 12, wherein the pin is formed by the outer wall.

14. The assembly of claim 1, further including a lens fixed relative to the light source, the lens comprising a concave surface receiving radiation from the light source and one of a planar and a convex surface directing the received radiation toward a target.

15. The assembly of claim 14, wherein the planar surface is disposed at an angle relative to the substrate.

16. The assembly of claim 1, further including a lens fixed relative to the light source, the lens comprising a planar surface receiving radiation from the light source, and one of a planar surface and a convex surface directing the received radiation toward a target.

17. The assembly of claim 16, wherein the planar surface is disposed at an angle relative to the substrate.

18. The assembly of claim 1, further including a lens fixed relative to the light source, the lens comprising a saddle-shaped surface receiving radiation from the light source and a planar surface directing the received radiation toward a target, the planar surface being disposed at an angle relative to the substrate.

19. The assembly of claim 1, further including a lens defining a first surface receiving radiation from the light source, a second surface directing the received radiation toward a target, and a mounting surface fixed to the substrate.

20. A method of manufacturing a light assembly for a hand-held medical diagnostic instrument, comprising:
   (a) providing an led mounted to a substrate, the substrate having a pair of electrical terminals;
   (b) mounting and electrically connecting the electrical terminals of the substrate to corresponding electrical terminals of a circuit board of the light assembly;
   (c) thermally connecting the electrical terminals of the substrate to a heat sink of the light assembly; and
   (d) connecting a lens to the substrate, a portion of the lens being supported by the heat sink.

21. The method of claim 20, further including electrically insulating the electrical terminals of the substrate from the heat sink.

22. The method of claim 20, further including overlaying the electrical terminals of the substrate, the heat sink, and a portion of the circuit board with an electrically insulative thermal conductor.

23. The method of claim 20, wherein the heat sink comprises a cylindrical housing having an open end, the method further including connecting an alignment pin to an outer wall of the housing at a predetermined distance from the open end, and mounting the substrate within the pinned housing.

24. A light assembly for a hand-held medical diagnostic instrument, comprising:
  (a) a thermally conductive cylindrical housing defining an open end;
  (b) a lens disposed proximate the open end;
  (c) an led mounted to a substrate and fixed relative to the lens, the substrate defining a pair of electrical terminals;
  (d) a light assembly circuit board disposed within the housing, the electrical terminals mounted and electrically connected to the circuit board; and
  (e) an electrically insulative thermal conductor thermally connecting the electrical terminals to the housing.

25. A method of forming a lens for a hand-held medical diagnostic instrument, comprising:
  (a) providing a mold body having a first end, a second end, and a cavity between the first and second ends, the cavity configured to receive a flow of lens material;
  (b) connecting a first insert to the first end such that an optical surface of the first insert is fluidly connected to the cavity, the optical surface of the first insert being one of planar and concave;
  (c) connecting a second insert to the second end such that an optical surface of the second insert is fluidly connected to the cavity, the optical surface of the second insert being one of planar, concave, and saddle-shaped; and
  (d) filling the cavity with the flow of lens material to form the lens, the optical surfaces of the first and second inserts forming corresponding optical surfaces on the lens.

* * * * *